(12) United States Patent
Gekhter et al.

(10) Patent No.: US 6,446,640 B1
(45) Date of Patent: Sep. 10, 2002

(54) DENTAL HYGIENE DEVICE WITH EASILY MOUNTED AND IDENTIFIED DENTAL HYGIENE ELEMENT

(75) Inventors: Vladimir Gekhter; Christopher J. Stvartak, both of Skokie; Kevin G. Yost, Winnetka, all of IL (US)

(73) Assignee: John O. Butler Company, Chicago, IL (US)

( * ) Notice: Subject to any disclaimer, the term of this patent is extended or adjusted under 35 U.S.C. 154(b) by 0 days.

(21) Appl. No.: 09/274,191

(22) Filed: Mar. 22, 1999

(51) Int. Cl.⁷ .............................. A45D 44/18; A61C 3/00
(52) U.S. Cl. ........................ 132/309; 132/310; 433/147
(58) Field of Search ................................ 132/309, 310, 132/321, 323, 324; 433/146, 147; 601/139, 141; 15/167.1

(56) References Cited

U.S. PATENT DOCUMENTS

| | | | | |
|---|---|---|---|---|
| 4,033,007 A | * | 7/1977 | Hadary | 15/172 |
| 4,572,223 A | * | 2/1986 | Rosenfeld | 132/309 |
| 4,710,996 A | * | 12/1987 | Tarrson et al. | 132/309 |
| 4,780,923 A | * | 11/1988 | Schultheiss | 433/147 |
| 5,313,684 A | * | 5/1994 | Fitjer | 15/167.1 |
| 5,328,370 A | * | 7/1994 | Chen | 433/147 |
| 5,934,295 A | * | 8/1999 | Gekhter et al. | 132/309 |
| 5,940,923 A | * | 8/1999 | Gunning | 132/309 |

* cited by examiner

Primary Examiner—John J. Wilson
Assistant Examiner—Robyn Kieu Doan
(74) Attorney, Agent, or Firm—Michael Best & Friedrich, LLC

(57) ABSTRACT

The present invention relates to dental hygiene devices carrying dental hygiene elements and to a method for assembling them. The dental hygiene devices have two intersecting cavities, with a dental hygiene element positioned in one cavity and a plug positioned in the other cavity. The plug engages a portion of the stem, thereby locking the dental hygiene element in place in the device.

28 Claims, 4 Drawing Sheets

DENTAL HYGIENE DEVICE WITH EASILY MOUNTED AND IDENTIFIED DENTAL HYGIENE ELEMENT

FIELD OF THE INVENTION

The present invention relates generally to dental hygiene devices. More particularly, this invention relates to a device carrying a dental hygiene element that is easy to assemble and that allows the user to easily identify the dental hygiene element mounted to the device. Additionally, this invention relates to a method for conveniently assembling dental hygiene elements to dental hygiene devices.

BACKGROUND OF THE INVENTION

Various devices are known in the art for cleaning and stimulating the teeth and gums to maintain good dental hygiene. The most ubiquitous of such devices is the conventional toothbrush. Another popular cleaning and stimulating device is an interproximal toothbrush such as one of the many different interproximal toothbrushes available from John O. Butler Company of Chicago, Ill. Still other types of commonly used cleaning and stimulating devices are rubber stimulators and picks mounted in appropriate handles.

A dental hygiene device thus comprises a brush or other cleaning or stimulating element attached to the handle of the device. The present invention is applicable to dental hygiene devices such as those designed with a brush or other element mounted to a separate carrying member that is removably attached to a handle. One such device is described in U.S. Pat. application Ser. No. 08/057,195 which is entitled "Dental Hygiene System," filed Mar. 8, 1998 and assigned to the present assignee, John O. Butler Company, and which is incorporated herein by reference. The present invention is also applicable to conventional dental hygiene devices having an element that is mounted to a handle comprising a single, integral unit. Assembly of the brush or other cleaning or stimulating element to the dental hygiene device is accomplished by permanently securing a stem or other part of the element either to a portion of the handle of the device, as in the latter case, or to a separate carrying member that is removably attached to the handle, as discussed above.

Cleaning or stimulating elements come in a variety of sizes and shapes. However, in all cases, these elements are small because they are intended for use in the mouth. As a result, properly assembling the brush or other cleaning or stimulating element either directly to the dental hygiene device or to a separate, removable carrying member can be a delicate and challenging process.

Properly and reliably securing the stem of the brush or other cleaning or stimulating element to the handle of the dental hygiene device or to a removable carrying member is important because in use these elements are subject to substantial pull-out forces. The conventional method of permanently assembling the brush or other element to the handle of the dental hygiene device is to make the handle or removable carrying member out of plastic and to mold the plastic around the stem of the element as the handle or removable carrying member is formed. This allows the plastic to closely conform to the shape of the stem, generally retaining it securely.

Nonetheless, under certain circumstances the stem may work its way out of its support. For instance, the stem used with many dental hygiene elements consists of two elongated wires twisted around each other in a spiral configuration. This twisted wire stem may "unscrew" from the molded plastic around it under extreme circumstances. This tendency of the stem to work its way out of its support may be minimized by providing a bend in the stem before molding.

As those skilled in the art will recognize, accurately positioning the stem in the mold is very difficult. The process, whether done by hand or by robotics, is cumbersome and time-consuming because of the difficulty of picking up the stem of the small element and properly orienting it in the mold. The process is even more difficult if the stem is bent to aid retention, as discussed immediately above. Locating the stem in its proper place in the mold is essential, because the mold may be damaged if the element is misaligned and lays across the parting line when the mold closes. Also, if brushes or elements with stems of various diameters are to be used, these variations must be accommodated.

Accordingly, the development of a method for permanently assembling a dental hygiene element to the handle of a dental hygiene device or to a removable carrying member that is easier, faster and more economical than presently available methods would be highly desirable. This method of assembly should allow the stem of the brush or other cleaning or stimulating element to be secured to the handle or to the removable carrying member in a manner that increases its resistance to pull-out. Further, this technique should be able to accommodate brushes or elements with stems of varying diameters.

Moreover, once the handle of the dental hygiene device or the removable carrying member has been completely assembled, the consumer or user should be able to easily identify the brush or other element mounted to it, particularly where identification of the element itself is difficult because of its overall small size and because variations among different elements of the same type are subtle and difficult to perceive.

Accordingly, one object of this invention is to provide a method of assembling a brush or other cleaning or stimulating element to the handle of a dental hygiene device or to a removable carrying member that is easier, faster and more economical than conventional methods of manufacture.

A further object of this invention is to provide a method of securing the stem of a brush or other cleaning or stimulating element to the handle of the dental hygiene device or to a removable carrying member in a manner that firmly holds the stem in place and thereby increases the retention of the stem in the device.

Yet another object of this invention is to provide a method of assembling a brush or other cleaning or stimulating element to the handle of a dental hygiene device or to a removable carrying member that accommodates brushes or elements with stems of different diameters.

SUMMARY OF THE INVENTION

The present invention involves providing a dental hygiene device with first and second intersecting cavities in the area which is to receive the stem of a brush or other cleaning or stimulating element. Preferably, the first and second cavities are generally perpendicular. The stem of the brush or other element is inserted into the first cavity and a plug is inserted into the second cavity to engage with and lock the stem in place. Preferably, the stem is either pre-bent to accept the plug or bent by the plug itself to enhance retention of the brush or other element. Finally, plugs may be provided with heads of different colors or different shapes corresponding to a particular feature of the brush or other element that is otherwise difficult to visually perceive.

BRIEF DESCRIPTION OF THE DRAWINGS

The above as well as other objects and advantages of the invention will become apparent from the following detailed description of the preferred embodiments in which reference is made to the accompanying drawings in which.

DESCRIPTION OF THE PREFERRED EMBODIMENTS

Figure 1:
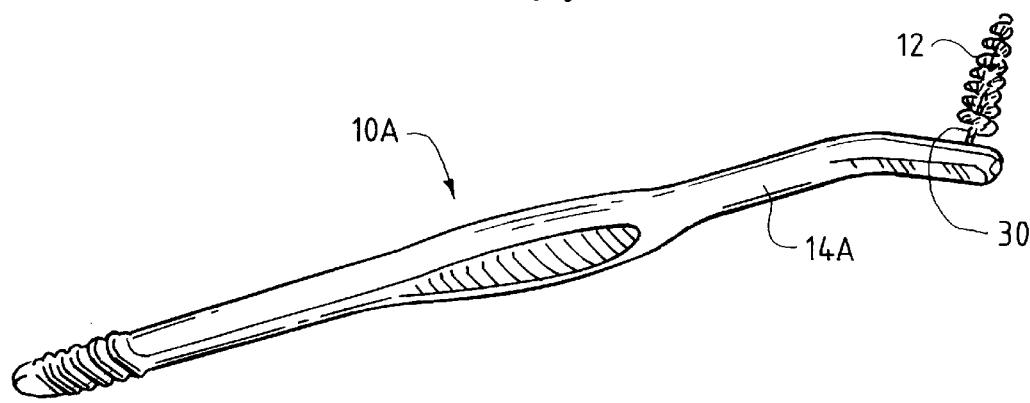
FIG. 1 is a perspective view of a dental hygiene device in accordance with the present invention showing an element mounted to a handle comprising a single, integral unit.
Figure 2:
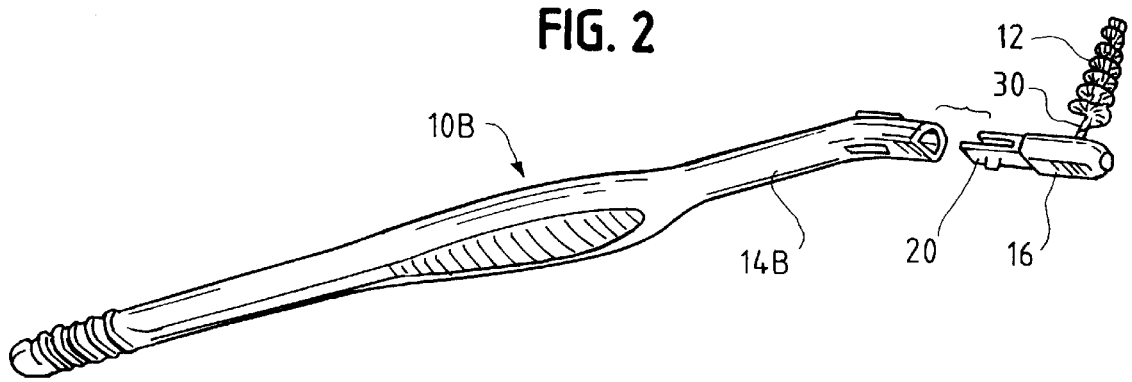
FIG. 2 is an exploded perspective view of a dental hygiene device in accordance with the present invention showing a removable carrying member positioned for attachment to a handle.

FIGS. 1 and 2 depict two different embodiments of dental hygiene devices 10A and 10B in accordance with the present invention. FIG. 1 depicts dental hygiene device 10A as having element 12 mounted to a handle 14A that comprises a single, integral unit. FIG. 2 depicts dental hygiene device 10B having a separate carrying member 16 to which element 12 is mounted and which is removably attachable to handle 14B. Where device 10B includes removable carrying member 16 and handle 14B, the carrying member and handle may be configured so that the carrying member is capable of attachment to and detachment from the handle by way of engagement portion 20, all in accordance with the teaching of John O. Butler Company's U.S. patent application Ser. No. 08/057,195, entitled "Dental Hygiene System" and filed Mar. 8, 1998, which is incorporated herein by reference.

Handle 14A as well as handle 14B and carrying member 16 may be made of any durable injection moldable thermoplastic including polypropylene, polyester or nylon. Alternatively, the handles or carrying member may be made of metal such as stainless steel. Preferably, however, polypropylene will be used.

Figure 3A:
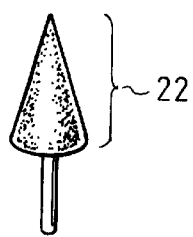
FIG. 3a is a perspective view of a stimulating element including an elongated stem.
Figure 3B:
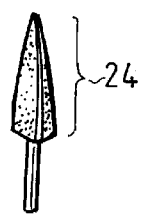
FIG. 3b is a perspective view of a pick including an elongated stem.
Figure 3C:
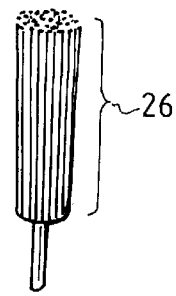
FIG. 3c is a perspective view of a single-tuft toothbrush including an elongated stem.

Although element 12 is depicted as an interproximal brush with a twisted wire stem, a variety of different cleaning and stimulating elements formed with or attached to a single elongated, flexible stem may be used. Alternative dental hygiene elements that may be mounted to distal end 18 include, for example, stimulating element 22 (FIG. 3a), pick 24 (FIG. 3b) and single-tuft toothbrush 26 (FIG. 3c). Besides the twisted wire stem depicted, other types of stems may be used including a solid wire stem, a solid or twisted wire stem encased in elastomer, and a plastic stem. In all cases it is important that the stem have sufficient give to permit it to bend, as described below. Preferably, the stem should be capable of taking a permanent bend either prior to or during assembly.

Figure 4:
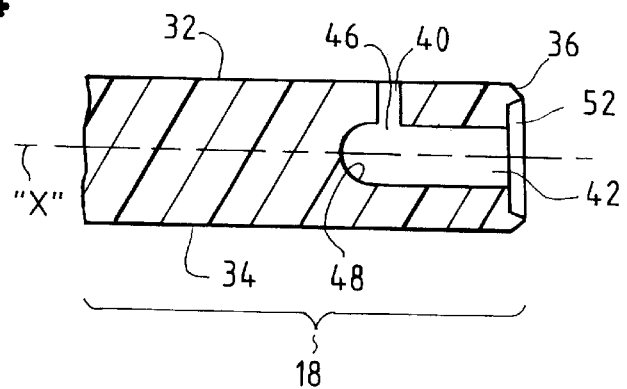
FIG. 4 is a partial elevation view, in cross-section, of the distal end of the handle of FIG. 1 or the distal end of the carrying member of FIG. 2 showing intersecting cavities in accordance with the present invention.
Figure 5:
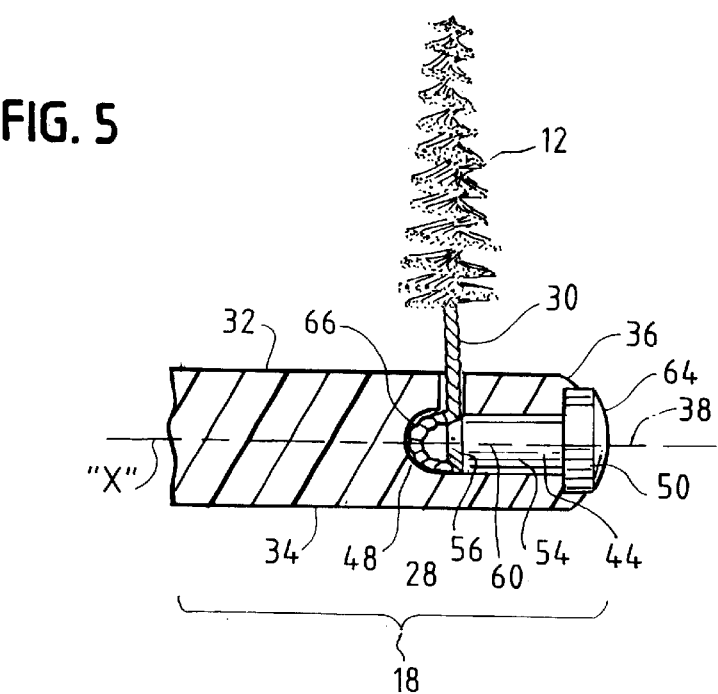
FIG. 5 is a partial elevation view, in cross-section, corresponding to FIG. 4 in which an interproximal brush has been assembled in the distal end of the handle of FIG. 1 or the distal end of the carrying member of FIG. 2 in accordance with the present invention.

FIGS. 4 and 5 illustrate a portion of the distal end 18 of carrying member 16 of dental hygiene device 10B. Since the distal end of dental hygiene device 10A would be identical for present purposes, the discussion which follows should be taken to apply as well to dental hygiene device 10A. Thus, although element 12 is shown in FIG. 5 with distal end 28 of its flexible twisted wire stem 30 mounted to distal end 18 of device 10B, element 12 would be mounted directly to handle 14A of device 10A in the same fashion.

Referring to FIG. 4, distal end 18 of device 10B has an upper surface 32, a bottom surface 34, and a rounded end surface 36 at its distal tip 38 (FIG. 5). Distal end 18 may be of any size and shape that can accommodate the diameter and length of cavities 40 and 42, which are discussed below, such as a "D-shaped" configuration, a circle, an oval, a rectangle and the like.

Distal end 18 has a first cavity 40 for receiving stem 30 and a second cavity 42 for receiving a plug 44 (FIG. 5). Preferably, the first cavity is configured as a bore to accommodate the generally circular diameters of conventional brush element stems. First cavity 40 passes through upper surface 32 of distal end 18 near rounded end surface 36 and extends downwardly through common opening 46 toward bottom surface 34 of the handle. First cavity 40 and second cavity 42 meet at common opening 46 (FIG. 4) at an angle of about 45 to 135 degrees. Preferably, the first and second cavities meet at a generally right angle. Although in FIG. 4 the first cavity is depicted as terminating at common opening 46, the first cavity may also extend beyond the second cavity, and indeed, may extend completely through to bottom surface 34.

Second cavity 42 extends inwardly from rounded end surface 36, meets and extends beyond first cavity 40, and terminates at a depression 48 which is preferably rounded as shown. Preferably, second cavity 42 extends from the center of distal tip 32 along longitudinal axis "x" of distal end 18 so that the second cavity meets the first cavity at the preferred right angle.

Figure 6:
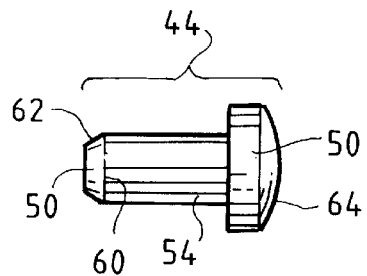
FIG. 6 is an elevation view of the plug intended for assembly with the dental hygiene device of the present invention.

Second cavity 42 is depicted in the Figures as a bore that can receive plugs having generally circular diameters, such as plug 44 shown in FIG. 6. However, the second cavity may have any size and shape that corresponds to the size and shape of the plug intended for insertion into the second cavity, which will facilitate alignment of the plug as it is inserted into the second cavity. Preferably, plug 44 will be provided with an expanded head 50, as is discussed below. Thus, second cavity 42 as depicted is undercut near end surface 36 of distal end 18 to form a dish-like cavity 52 (FIG. 4) to facilitate the locating and seating of plug 44, including its expanded head (FIG. 5). Alternatively, however, second cavity 42 may be formed with a constant diameter.

Referring now to FIG. 6, plug 44 has a shaft 54 with a preferably generally circular cross-section. However, shaft 54 may be provided with a variety of shapes, such as a triangle, square, rectangle and the like. Preferably, the diameter of shaft 54 of the plug either corresponds to the diameter of the second cavity, or is slightly larger, so that when plug 44 is pressed home into the second cavity, it will remain in place by means of a friction fit. Alternatively, plug 44 may be secured in place in second cavity 42 by means of adhesive, ultrasonic welding or other conventional methods of attachment. In all cases, shaft 54 of plug 44 must be long enough to extend at least partially across common opening 46. Preferably shaft 54 of plug 44 (FIGS. 4 and 5) extends beyond the common opening into depression 48.

Shaft 54 has an engagement section 56 at the distal tip 60 of the shaft, and preferably an expanded head 50. Of course, the head need not be expanded and may simply comprise the distal end of a constant diameter shaft. Engagement section 56 preferably includes a bevel 62 at distal tip 60 of the shaft of the plug. This embodiment is preferred because it facilitates insertion of the plug into second cavity 42 and because it increases the surface area of the engagement section which contacts distal end 28 of stem 30. Alternatively, however, the distal end of engagement section 56 may comprise a flat surface that is generally perpendicular to the longitudinal axis of the plug.

Preferably, the head of the plug that is chosen for insertion is provided with either a color or a shape corresponding to a feature of the dental hygiene element inserted into the first cavity that is difficult to visually perceive. These subtle features include, for example, the diameter of stem 30 of element 12 or the shape of brush element 12. In this way, the user can easily identify the size or type of the dental hygiene element positioned in the device by looking at the color or shape of top surface 64 of the head of the plug.

Figure 7A:
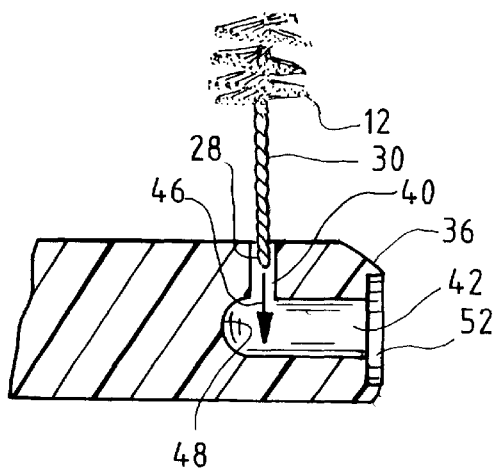
FIGS. 7a–7e are cross-sectional views of a portion of the dental hygiene device of the present invention showing successive stages of one method by which the dental hygiene device is assembled.
Figure 7B:
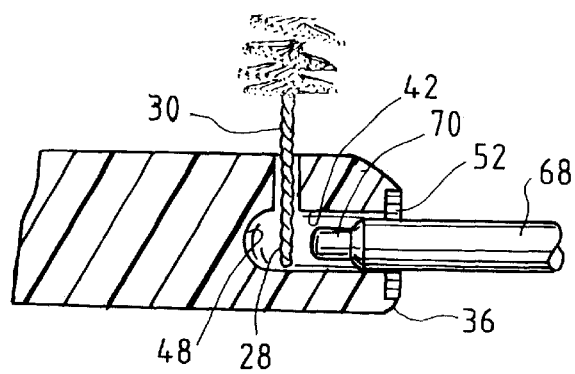
Figure 7E:
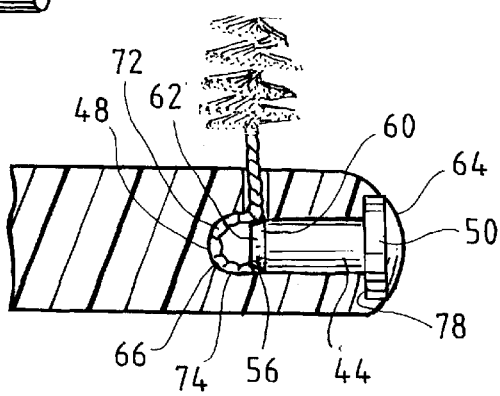
Figure 8A:
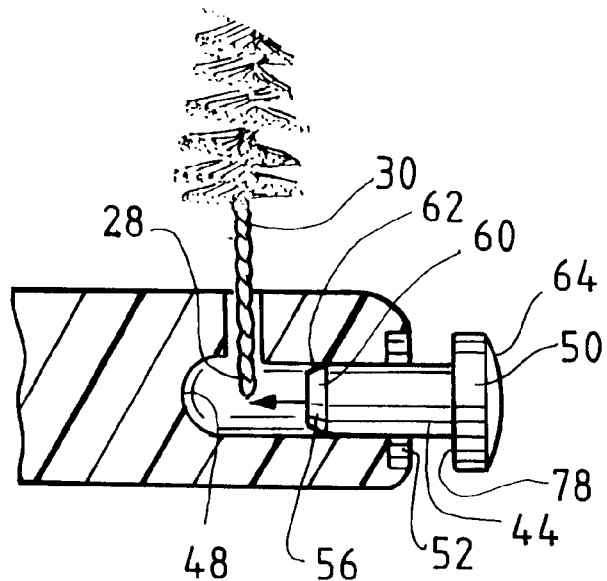
FIGS. 8a and 8b are cross-sectional views of an alternate embodiment of the invention corresponding generally to FIGS. 7d and 7e.
Figure 8B:
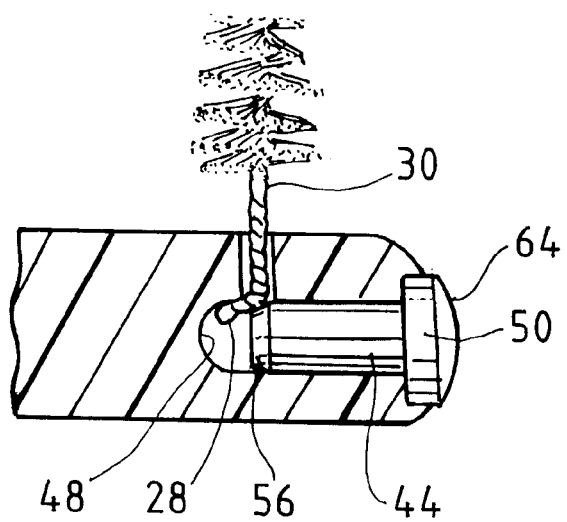

Stem 30 of element 12 is positioned in first cavity 40 so that distal end 28 of the stem crosses common opening 46 and at least partially extends into second cavity 42. Distal end 28 of the stem is bent so that it lies against depression 48 of the second cavity. Preferably, as shown in FIG. 5, distal end 28 is bent into a half-moon shape 66 that lies against rounded depression 48 of the second cavity. As explained below, preferably this bending is accomplished by a tool with a rounded leading edge that is inserted into the second cavity before the plug is inserted (FIGS. 7b and 7e) or, alternatively, by the inserted plug itself (FIGS. 8a and 8b). Also, where distal end 28 of stem 30 of element 12 only partially extends into second cavity 42 (FIG. 8a), the distal end 28 of the stem may be simply bent into depression 48 without forming the complete half-moon shape. In both cases, the bend in the distal end 28 of the stem decreases the tendency of twisted wire stems to untwist, and otherwise prevents all types of stems from working themselves out of handle 14A or carrying member 16.

The present invention also includes a method for assembling dental hygiene device 10, as depicted in FIGS. 7a–7e and FIGS. 8a and 8b. This method comprises first selecting a dental hygiene element having an elongated and flexible stem as described above. Preferably, a plug is also selected with a color or shape that corresponds to a difficult-to-perceive feature of the dental hygiene element, also as discussed above.

Figure 7C:
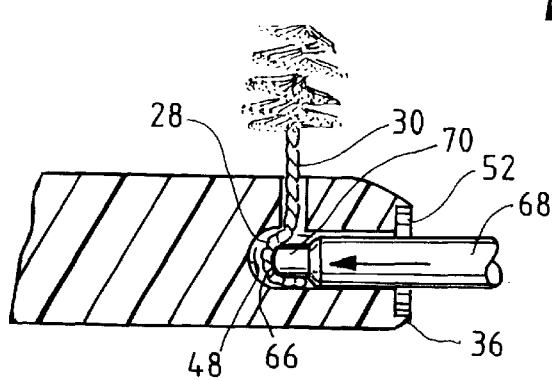

Stem 30 of element 12 is inserted into first cavity 40 (FIG. 8a). Distal end 28 of the stem extends at least partially into second cavity 42 and, preferably, as seen in FIG. 7b, distal end 28 extends across the second cavity. Preferably, tool 68 in the form of a metal rod having a proximal rounded tip 70 is driven into cavity 42 to form a half-moon bend in the distal end of stem 30 of element 12 by forcing the distal end of the stem to take the shape of rounded depression 48, as seen in FIG. 7c. Rounded tip 70 is undercut to facilitate entry into cavity 42 and, more importantly, to facilitate the formation of a smooth half moon bend 66 without causing undue distortion in distal end 28 of stem 30. Once distal end 28 is bent in this way, tool 68 is removed from second is cavity 42.

Figure 7D:
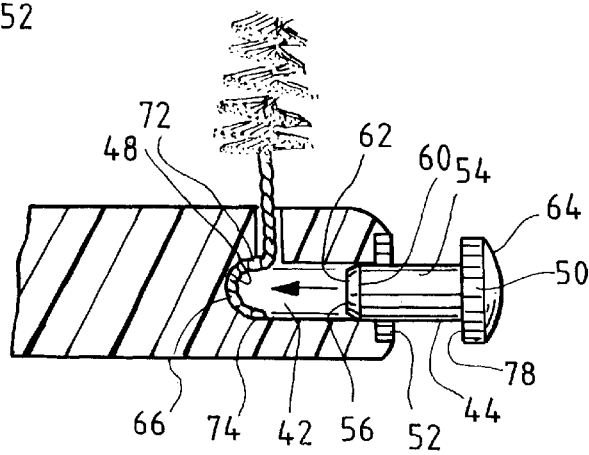

Turning next to FIG. 7d, plug 44 is then inserted into second cavity 42. Dish-like cavity 52 in second cavity 42 and bevel 62 in the engagement section 56 of the plug facilitate insertion of the plug by allowing the plug to be properly positioned and oriented and to easily enter the second cavity. The length of the shaft 54 of the plug is chosen so that as head 50 of the plug seats in dish-like cavity 52, engagement section 56 of plug 44 presses against the top portion 72 and bottom portion 74 of half moon bend 66 in the stem to lock the stem in place. The diameter of shaft 54 is slightly larger than the diameter of cavity 42 to insure a tight friction fit.

In an alternative embodiment, as depicted in FIGS. 8a and 8b, plug 44 may be inserted into the second cavity (FIG. 8a) so that the engagement section of the plug forces the distal end of stem 30 of element 12 to bend into the rounded depression 48 of the second cavity. The engagement section then abuts a portion of the distal end of stem 30, thereby locking the stem in place between the distal end of the plug and the top portion 76 of rounded depression to 48 of the second cavity (FIG. 8b).

In both cases, the head of the assembled plug lies within distal end 18. As a result, top surface 64 of the plug head and end surface 36 of the distal end form a smooth, continuous surface (FIG. 8a). On the other hand, the expanded head of the plug may lie outside of distal end 18, with the bottom surface 78 (FIG. 8b) of the head abutting outer surface 36 of the distal end. Also, a plug in which the head is not expanded may be used. In all of these embodiments, however, the top surface 64 of the head of the plug, and hence its color and shape, are exposed to view.

While the present invention is described above in connection with specific embodiments, the invention is intended to cover all alternatives, modifications or equivalents that may be included within its sphere or scope, as defined by the appended claims.

What we claim is:

1. A dental hygiene device carrying a dental hygiene element comprising:

a dental hygiene device;

with a flexible stem;

a dental hygiene element;

a first cavity at the distal end of the device containing the stem of the dental hygiene element and a second cavity containing a plug, the second cavity intersecting the first cavity;

the second cavity extending beyond the first cavity and terminating in a depression and the distal end of the flexible stem of the dental hygiene element following the contour of the depression; and the plug having an engagement section at its distal tip, the plug being secured in the second cavity with its engagement section extending into the first cavity and abutting a portion of the stem of the dental hygiene element at the intersection of the depression and the first cavity to lock the stem in place in the device.

2. The dental hygiene device of claim 1 in which the device includes a handle comprising a single, integral unit.

3. The dental hygiene device of claim 1 in which the device includes a separate carrying member for holding the dental hygiene element and a handle, the carrying member being removably attachable to the handle.

4. The dental hygiene device of claim 1 in which the dental hygiene element is selected from the group consisting of interproximal brushes, stimulating elements, picks, single-tuft toothbrushes, and compliant cleaning devices.

5. The dental hygiene device of claim 1 in which the stem of the dental hygiene element is selected from the group consisting of twisted wire stems, solid wire stems, wire stems encased in elastomer and plastic stems.

6. The dental hygiene device of claim 1 in which the device is made of a durable injection moldable thermoplastic from the group consisting of polypropylene, polyester and nylon.

7. The dental hygiene device of claim 1 in which the first cavity and second cavity intersect at an angle of about 45 to 135 degrees.

8. The dental hygiene device of claim 1 in which the first cavity and second cavity intersect at a generally right angle.

9. The dental hygiene device of claim 1 in which the first cavity extends beyond the second cavity.

10. The dental hygiene device of claim 1 in which the second cavity is disposed at the center of the distal tip of the device.

11. The dental hygiene device of claim 1 in which the depression is rounded.

12. The dental hygiene device of claim 1 in which the size and shape of the second cavity corresponds to the size and shape of the plug.

13. The dental hygiene device of claim 2 in which the plug has an expanded head and the second cavity is undercut to form a dish-like cavity near the surface of the device for receiving the expanded head.

14. The dental hygiene device of claim 1 in which the plug is secured in the second cavity by means of a friction fit.

15. The dental hygiene device of claim 1 in which the plug is secured in the second cavity by means selected from the group consisting of adhesive and ultrasonic welding.

16. The dental hygiene device of claim 1 in which the engagement section at the distal tip of the plug is beveled.

17. The dental hygiene device of claim 1 in which the head of the plug is provided with a color corresponding to a selected feature of the dental hygiene element positioned in the first cavity.

18. The dental hygiene device of claim 1 in which the head of the plug is provided with a shape corresponding to a selected feature of the dental hygiene element positioned in the first cavity.

19. The dental hygiene device of claim 1 in which the stem is sufficiently long so that its distal end extends completely across the second cavity.

20. The dental hygiene device of claim 11 in which the stem is bent in the form of a half moon bend to correspond to the rounded depression.

21. A dental hygiene device carrying a dental hygiene element comprising:

a dental hygiene device;

with a flexible stem;

a dental hygiene element;

a first cavity at the distal end of the device containing the stem of the dental hygiene element and a second cavity containing a plug, the second cavity intersecting the first cavity at a generally right angle;

the second cavity extending beyond the first cavity and terminating in a depression and the distal end of the flexible stem of the dental hygiene element following the contour of the depression; and the plug having an engagement section at its distal tip, the plug being secured in the second cavity with its engagement section extending into the first cavity and abutting a portion of the stem of the dental hygiene element to lock the stem in place in the device.

22. A dental hygiene device carrying, at its distal end, a dental hygiene element with a flexible stem comprising:

a first cavity at the distal end of the device for receiving the stem of the dental hygiene element and a second cavity for receiving a plug, the second intersecting the first cavity, the dental hygiene element having a selected feature; and a plug having an engagement section at its distal tip, the plug being secured in the second cavity with its engagement section extending into the first cavity and abutting a portion of the stem of the dental hygiene element to lock the stem in place in the device, the plug having a head provided with a color or shape corresponding to the selected feature of the dental hygiene element positioned in the first cavity.

23. A method for assembling a dental hygiene device comprising:

providing a dental hygiene device with a first cavity and a second cavity at the distal end of the device, the second cavity intersecting the first cavity, the second cavity extending beyond the first cavity and terminating in a depression;

selecting a dental hygiene element having a flexible stem, the stem having a distal end;

selecting a plug having a head at its proximal tip and an engagement section at its distal tip;

positioning the stem of the dental hygiene element in the first cavity so that the distal end of the stem extends at least partially into the second cavity;

bending the distal end of the stem of the dental hygiene element by inserting a tool into the second cavity to bend the distal end of the stem into the depression of the second cavity so that it follows the contour of the depression; and inserting the plug in the second cavity so that the engagement section of the plug presses against a portion of the distal end of the stem to lock the stem in place in the device.

24. The method of assembling a dental hygiene device of claim 23, in which the second cavity terminates in a rounded depression and the bending is accomplished by inserting a tool having a proximal tip that is undercut and rounded to force the distal end of the stem to take the form of a half moon bend.

25. The method of assembling a dental hygiene device of claim 24 in which the half moon bend in the distal end of the stem has top and bottom portions, and the engagement section of the plug inserted into the second cavity presses against the top and bottom portions of the half moon bend.

26. The method of assembling a dental hygiene device of claim 23 in which the plug is positioned in the second cavity so that the top surface of the plug and the surface of the device form a smooth, continuous surface.

27. The method of assembling a dental hygiene device of claim 23 in which the dental hygiene device has a selected feature and the head of the plug is provided with a color that corresponds to the selected feature of the dental hygiene device positioned in the first cavity of the device.

28. The method of assembling a dental hygiene device of claim 23 in which the dental hygiene device has a selected feature and the head of the plug is provided with a shape that corresponds to the selected feature of the dental hygiene device positioned in the first cavity of the device.

* * * * *